(12) United States Patent
Kisty

(10) Patent No.: US 10,857,486 B2
(45) Date of Patent: Dec. 8, 2020

(54) SIDE-STREAM FOAM MONITOR AND CONTROL SYSTEM

(71) Applicant: Solenis Technologies, L.P., Schaffhausen (CH)

(72) Inventor: Jeffrey J Kisty, Marlborough, MA (US)

(73) Assignee: SOLENIS TECHNOLOGIES, L.P., Wilmington, DE (US)

( * ) Notice: Subject to any disclaimer, the term of this patent is extended or adjusted under 35 U.S.C. 154(b) by 261 days.

(21) Appl. No.: 15/592,868

(22) Filed: May 11, 2017

(65) Prior Publication Data

US 2017/0348616 A1 Dec. 7, 2017

Related U.S. Application Data

(60) Provisional application No. 62/337,395, filed on May 17, 2016.

(51) Int. Cl.

| | |
|---|---|
| B01D 19/00 | (2006.01) |
| B01D 19/04 | (2006.01) |
| B01D 19/02 | (2006.01) |
| G01N 13/00 | (2006.01) |
| C12M 1/21 | (2006.01) |
| B05B 7/00 | (2006.01) |
| B05B 13/02 | (2006.01) |
| G01F 23/292 | (2006.01) |
| G01N 13/02 | (2006.01) |

(52) U.S. Cl.
CPC ......... *B01D 19/0063* (2013.01); *B01D 19/02* (2013.01); *B01D 19/04* (2013.01); *B05B 7/005* (2013.01); *B05B 13/0278* (2013.01); *C12M 41/02* (2013.01); *G01F 23/292* (2013.01); *G01N 13/00* (2013.01); *G01N 2013/025* (2013.01)

(58) Field of Classification Search
CPC .... B01D 19/0063; B01D 19/02; B01D 19/04; G01F 23/292
See application file for complete search history.

(56) References Cited

U.S. PATENT DOCUMENTS

| 3,107,519 A * | 10/1963 | McGinn | G01N 7/00 73/60.11 |
| 3,151,061 A * | 9/1964 | Orr | B01J 19/002 159/DIG. 4 |
| 3,739,795 A * | 6/1973 | Hyde | C10G 33/02 137/5 |

(Continued)

FOREIGN PATENT DOCUMENTS

| CN | 103833096 A | 6/2014 |
| CN | 204569471 U | 8/2015 |

(Continued)

OTHER PUBLICATIONS

Li et al. DERWENT abstract for CN 203556164.*

(Continued)

*Primary Examiner* — Michael A Salvitti
(74) *Attorney, Agent, or Firm* — Lorenz & Kopf, LLP

(57) ABSTRACT

Provided is a device which is capable of ongoing measurement of variable foaming tendencies in a fluid system and provide a signal to regulate the feed rate of defoamer accordingly to maintain foaming at an acceptable target level. The regulation of feed can be accomplished automatically or manually.

17 Claims, 1 Drawing Sheet

(56) References Cited

U.S. PATENT DOCUMENTS

| | | | |
|---|---|---|---|
| 4,624,745 A | 11/1986 | Sande et al. | |
| 4,859,987 A * | 8/1989 | Markus | F01M 11/12 340/450 |
| 4,978,471 A | 12/1990 | Starch | |
| 5,108,655 A * | 4/1992 | Johns, Jr. | B01D 19/04 162/45 |
| 5,375,459 A * | 12/1994 | Gerke | G01N 13/00 73/60.11 |
| 5,437,842 A * | 8/1995 | Jensen | B05B 12/122 422/105 |
| 5,465,610 A * | 11/1995 | Loisel | G01N 13/00 356/440 |
| 5,476,573 A * | 12/1995 | Hirose | C12M 29/02 202/197 |
| 5,597,950 A * | 1/1997 | Mullen | G01F 23/241 73/53.01 |
| 5,868,859 A * | 2/1999 | Hei | B01D 19/04 134/18 |
| 5,922,112 A * | 7/1999 | Zappi | B01D 19/04 95/155 |
| 6,397,665 B1 * | 6/2002 | Kirts | G01N 13/02 73/579 |
| 6,461,414 B1 * | 10/2002 | Kohl | E21B 43/12 95/1 |
| 6,640,618 B2 * | 11/2003 | Kirts | G01N 13/02 250/357.1 |
| 2001/0042407 A1 * | 11/2001 | Kirts | G01N 13/02 73/579 |
| 2002/0116137 A1 * | 8/2002 | Kirts | G01N 13/02 702/50 |
| 2006/0210139 A1 | 9/2006 | Carroll et al. | |
| 2007/0000488 A1 * | 1/2007 | Koerner | A61M 15/0085 128/203.15 |
| 2010/0310757 A1 * | 12/2010 | Ooshiro | B05C 5/0291 427/8 |
| 2011/0172343 A1 * | 7/2011 | Panz | B01D 19/0409 524/493 |
| 2013/0285821 A1 * | 10/2013 | Nakamura | G01N 1/2273 340/603 |
| 2016/0001200 A1 * | 1/2016 | Emkey | B01D 17/0214 210/776 |
| 2017/0348616 A1 * | 12/2017 | Kisty | B01D 19/02 |

FOREIGN PATENT DOCUMENTS

| | | |
|---|---|---|
| WO | 0114048 A1 | 3/2001 |
| WO | 2017200841 A | 11/2017 |

OTHER PUBLICATIONS

Taiwan Patent Office, Office Action issued in TW Application No. 106116229, dated Jul. 12, 2018.

European Patent Office International Searching Authority, International Search Report and Written Opinion for International Application No. PCT/US2017/032190 dated Jul. 26, 2017.

* cited by examiner

SIDE-STREAM FOAM MONITOR AND CONTROL SYSTEM

This application claims the benefit of U.S. Provisional Patent Application No. 62/337,395, filed on May 17, 2016, the entire contents of which are hereby incorporated by reference.

BACKGROUND

Industries and municipalities spend large sums of money to pay for chemicals used to control foam levels in their aqueous systems. The typical applications are industrial and municipal wastewater treatment plants, pipe lines, aerated lagoons, and process tanks, among others. The chemicals used are interchangeably called defoamers and antifoams. Their feed rates are typically controlled manually in response to a visual assessment of how much foam has accumulated in the process. Some methods of automated control have been proposed; however, most applications revert back to manual control due to flaws in the design and function of the automated processes. Manual and imperfect automatic control of defoamer feed lead to periods of underfeed and overfeed. This is especially true because the foaming behavior of many industrial fluid systems, such as those in paper mills, can change quickly depending on the upstream processes. Under-feed can result in excessive foam which effects abutting spaces, real estate, water ways, level sensing equipment, the ability to aerate the fluid system, as well as industrial process contamination.

There is, therefore, a tendency to overfeed defoamers to the point that there is no visible foam, even though a certain minimum level of foam may be tolerable. Additionally, because there is no foam to observe when the defoamer is over fed, overfeed conditions can go on undetected for long periods of time before being corrected. The expense of over feeding is costly, while underfeeding is unacceptable. In addition to cost, overfeeding can cause other problems in some systems—for example in paper mills excessive defoamer can result in sheet formation defects and increased dirt count. In fermentation industries, excessive defoamer can result in poor performance in the ultrafiltration systems.

It is, therefore, the object of this invention to provide a device which is capable of ongoing measurement of variable foaming tendencies in a fluid system and provide a signal to regulate the feed rate of defoamer accordingly to maintain foaming at an acceptable target level. The regulation of feed can be accomplished automatically or manually.

Also provided, is a device that is easy to adjust and calibrate the rate of foam formation to reasonably represent the behavior of the fluid system under study with a side-stream sample of such fluid system.

It is also among the objectives of this invention to provide an apparatus which is not susceptible to malfunction due to the accumulation of scum or plugging by solids and debris typically found in wastewater treatment applications.

It is further among the objectives of this invention to create a device which is simple to operate, using a bare minimum of utility types, and requiring little to no maintenance, making it suitable for industrial and municipal use in remote locations.

In its preferred method of use, this foam monitoring and control system a) draws a side-stream of the process fluid under study, as needed, either before or after the defoamer is added, b) synthetically generates and measures foam in a separate vessel or foam cell vessel, which maintains a constant fluid level to simulate the real-time behavior of foam generation in the fluid process under study, c) specifically measures the level of foam in the foam cell vessel with a non-contact optical distance measurement sensor, d) produces a signal with said optical distance measurement sensor, and e) uses the signal to regulate the feed rate of a defoamer to the process under study to control the foam level in specific areas of that process.

U.S. Pat. No. 3,107,519, relates to a laboratory bench test for measuring the amount of foam generated in a system by recirculating a small sample of a foaming fluid in a vessel and is not designed for a continuous once-through flow of a side-stream of the process fluid under study.

Devices that are typically used in the industry are contacting sensors that measures the foam amount, such as described in U.S. Pat. No. 5,437,842 A. This is done through the use of capacitance type proximity probes and electrical conductance probes. However, these can lead to flawed results due to the accumulation of foam deposits (residue build up) requiring regular cleaning to maintain their efficacy. False foam levels are frequently encountered with probe-type foam sensing devices. The current method uses an optical distance measurement sensor wherein light is reflected from the surface of the foam and therefore does not require cleaning.

Many foam sensing and control devices used today are focused on using contacting foam sensing devices. Unfortunately, these are generally ineffective when the fluid level in the process changes or turbulence results in an uneven fluid level. Because of the inherent variations in the process which are not related to foaming, a signal from a contacting sensor is not directly related to the foaming tendency of the process fluid. As a result, any control scheme tied to such a signal can lead to loss of foam control.

By contrast, the current methods use a side-stream of the process fluid that is fed into a vessel through an opening in the top and exiting through an outlet or drain in the bottom of the vessel, while maintaining a controlled and stable fluid level. This enables the foam sensing device to accurately simulate and measure the foam generating behavior of the process fluid system under study regardless of physical changes in that system.

U.S. Pat. No. 3,739,795A references sampling a side-stream of the process fluid. An upward fluid flow is taught, creating a challenge to maintain a constant fluid level and retain the foam that is generated. In this method the fluid is drained from the side, creating an asymmetrical flow pattern that can remove the foam which is to be measured within the vessel. Contact probes are used to sense the level of the foam and are subject to the problems associated with fluid contact discussed above. By contrast, the current method uses a non-contact optical distance measurement sensor, which requires no cleaning.

These types of previously used methods have used compressed air that is bubbled or sparged through the fluid to create foam. However, there are problems associated with using compressed air, such as, accuracy, repeatability and maintenance issues. Compressed air also adds another utility to the process which increases complexity, cost, and maintenance to the operation. The accuracy associated with using compressed air to generate the foam under controlled conditions relies on the function of a compressor, pressure regulator, air flow meter, fluid flow meter, and a controlled orifice size.

Any of these devices using compressed air can affect the bubble size and quantity of foam being generated and measured. Aerating stones, spargers, and the like are also subject to scale formation around the orifices resulting in deposits which affect the reliable flow of air through them. The current method does not use compressed air but forms and accumulates foam simply through the natural and unchanging effect of cascading a constant fluid flow into a tube within a stationary cup. This method improves the reliability and repeatability of the system. The method used in this invention simulates the industrial processes where air is introduced from the bottom.

Attempts to regulate the amount of defoamer used by allowing foam to accumulate to a level which activates a sensor, then adding a preset timed addition of defoamer to "knock down" the foam has been unreliable. Allowing foam to substantially accumulate before knocking it down creates an opportunity for the foam to stabilize, thus making it more difficult breakdown with a defoamers. Defoamers are typically silica based and do not have persistence in the process.

The preferred use of this invention uses an optical-sensor in combination with a microprocessor based proportional and integral control loop (PID loop). We are therefore able to accurately measure the foam in real time and feed a commensurate amount of defoamer which is proportional to foamability of the fluid system. This invention therefore does not require special defoamer formulations which are good at "knock-down" and broadens the selection of suitable products available to the end user.

SUMMARY OF THE INVENTION

Provided is a method for the measurement and control of foaming in fluid processing applications. The method uses a side-stream of a process fluid stream being treated with defoamer, to simulate the foaming behavior of that fluid by cascading it into a specially designed vessel or foaming cell and measuring the foam level with an optical distance measurement sensor. The measurement sensor produces a signal which is used to regulate the feed rate of a foam control chemical to the process fluid stream under study.

For some fluids which do not foam readily, it may be preferable but not necessary, for an aspirator to be installed on the side-stream line feeding the process fluid to the foam cell or vessel for generating the foam. An aspirator is an in-line device which educts air into the fluid stream by creating a vacuum by causing a pressure drop.

Provided is a method for monitoring and controlling foaming of a process fluid stream. The current method uses a side-stream of the process fluid stream under study, which is drawn or pumped through a sample line to a vessel or foam cell having an open top or inlet and a drain or outlet. The process fluid of the side stream sample can be passed through the foam cell one or more times as necessary. The process fluid of the side stream is directed downward through the opening of the foam cell where bubbles become entrained within the foam cell vessel due to the process fluid being maintained at a constant level within the foam cell vessel.

The monitoring and control system can be further configured to include an inner cup within the foam cell vessel and a tube or pipe that is suspended above and extending into the inner cup. The process fluid from the side stream is directed through the tube or pipe and into the inner cup of the foam cell vessel. Bubbles are entrained in the cup section where they may result in foam. The bubbles and fluid change direction as a result of the placement of the cup, and consequently flow upward over the lip of the inner cup, resulting in foam build up on the process fluid surface within the foam cell vessel. An optical distance measurement sensor located above the foam cell measures the foam level and produces a proportional electronic level output signal.

Foam cell and foam cell vessel is used interchangeably throughout the application and signifies the vessel in which the side stream of process fluid is delivered.

DETAILED DESCRIPTION

Figure 1:
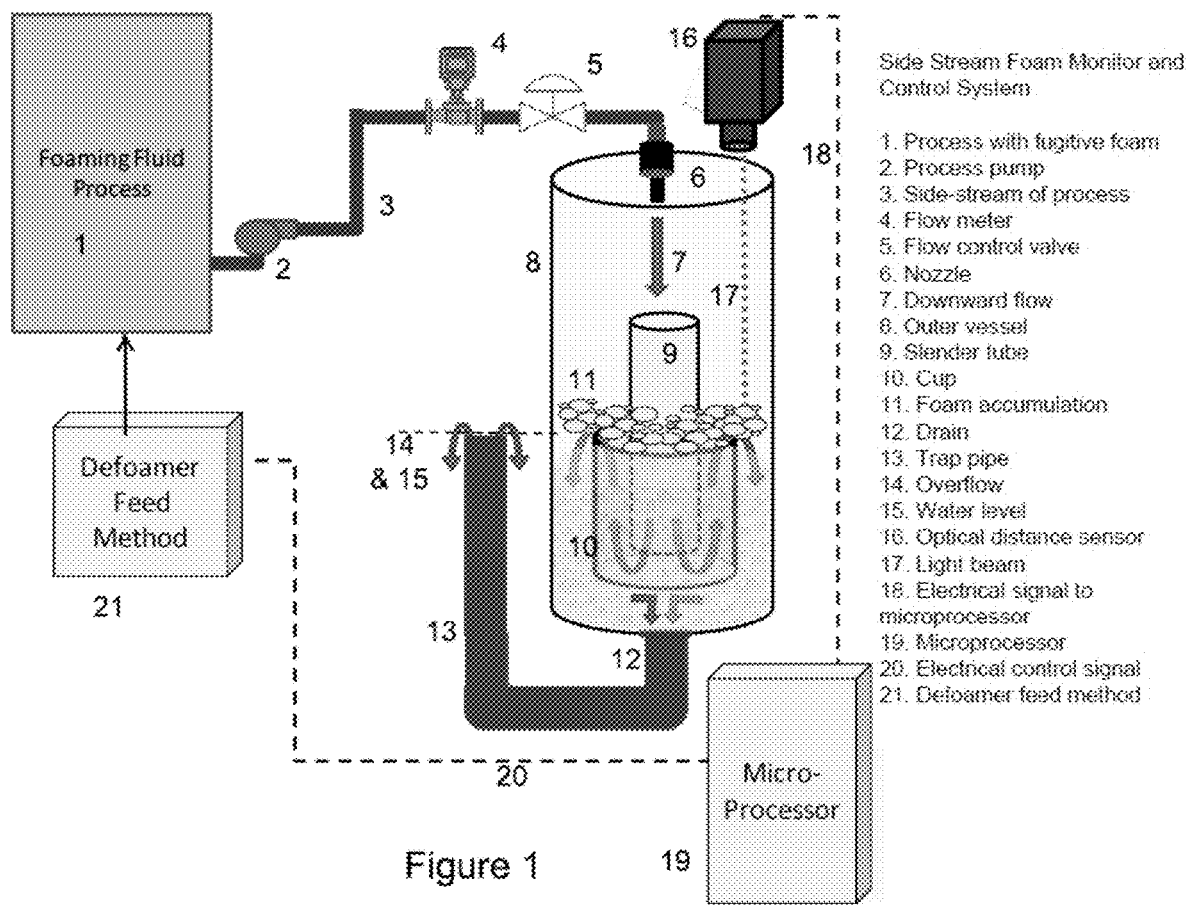
FIG. 1, is a schematic of one variation of the current method for the monitoring and control of foaming in aqueous processes.

In one aspect, the current method uses a side-stream of a fluid stream under study, at which point the defoamer feed may or may not precede the sample point, to simulate the foaming behavior of that fluid.

A side-stream refers to a portion of the process fluid stream having either a continuous or in intermittent flow. For example, the flow rate of a process fluid stream to a flow cell vessel, such as a 20 centimeter diameter sized cylinder, a monitoring and control system may be in the range of from about 3.78 liters (L) to about 60 liters per minute. However, systems may be smaller or larger, for example, smaller systems may use flow rates as low as 500 milliliters per minute or much larger systems that may use up to 760 liters per minute.

Fluid refers to any aqueous medium found in water processing plants and papermills. More particularly, the process fluid can have a specific conductance of between 0.01 and 130 milliseimens per centimeter (mS/cm), a pH in the range of 2 to 14, suspended solids in the range of from 0 to about 60%, and total dissolved hardness in the range of 1 to 11,000 milligrams per liter (mg/L) as calcium carbonate.

Defoamer refers to classifications of many types of chemicals used either as blends or singularly. Defoamers are also known as antifoam, which are used to suppress the foaming behavior of a fluid. In practice, defoamers are comprised of individual compounds or blends of compounds which contain for example, silica, silicone, fatty alcohols, waxes, glycols, oils, EBS, surfactants, hydrocarbons, emulsifiers, fatty esters, alcohols, alcohol ethoxylates, alcohol propoxylates and water.

In some aspects of the above methods, the side-stream of process fluid is directed into a foam cell vessel wherein the fluid cascades into the foaming vessel, which entrains air to create a level of foam on the water surface where the foam height is measured with a non-contact optical distance measurement sensor.

In other aspects of the above methods, the term "optical-sensor" refers to the class of optical measuring devices which work by emitting light, reflecting it off of a surface to be measured and detecting the return of light with a light receiving element called the sensor. The light type that may be used shall be within the wavelength range of 390 to 780 nanometers. These devices go by many names, some are called laser distance sensors, laser measurement sensors, laser range finders, all-purpose laser sensors and the like. There are several types of suitable detection configuration methods for distance measurement which include: Triangulation, time of flight, pulsed time of flight, multiple frequency phase-shift, modulated beam, and interferometry. The spot diameter of the light used may be adjustable to improve sensitivity.

In other aspects of the current method, the non-contact optical distance measurement sensor (16) can be a "reflective model-photoelectric sensor". This is a reflective type photoelectric sensor consisting of two elements: a light emitting element and a light receiving element. The photoelectric sensor emits a light beam (visible or infrared) from its light emitting element. The light beam is reflected from the surface of a target and received by the light receiving element. The distance from the target surface to light receiving element is determined through triangulation or time of flight (TOF), depending on the type of receiving element used.

In some aspects of the current method, the optical sensor can be an All Purpose Laser-Sensor of 660 nanometer wave length (red laser), class 2, model LR-TB5000 made by Keyence. This laser uses time of flight technology and can regulate the feed rate of defoamer being added to the process fluid stream.

In some aspects of the current method, the non-contact optical distance measurement sensor in combination with the microprocessor based proportional and integral control loop (PID loop), provides for the accurate measurement of accumulating foam in real time and the ability to feed a commensurate amount of defoamer which is proportional to foamability of the fluid system.

The method can also use the electronic signal from the optical measuring device, which is proportional to a range of the foam level and consequently controls the defoamer delivered proportionally, or the electronic signal can trigger a digital (on/off) signal to the defoamer feed which occurs when the foam level transitions through one or several level set points. A level set point is defined as a specific foam height target which causes a control response which can be any number of actions such as an alarm or an automated increase or decrease in defoamer feed rate.

The electronic signal can be also be transferred to a microprocessor that controls or regulates the amount of defoamer delivered to the process fluid stream. Or, the electronic signal may be used as a guide to make manual adjustments to the addition of defoamer. It can also be used to regulate a mechanical feeding device directly.

The method can use the proportional signal from the optical distance measurement sensor, which may be conditioned with a microprocessor to produce various control strategies with which to modify the feed of the defoamer to strategic points in the process. Control strategies include but are not limited to proportional control through proportional-integral-derivative control, also known as PID control, as well as other timed feed strategies.

In referring to FIG. 1, there is provided an outer cylindrical vessel (8) having an opening or inlet (6) at the top of the vessel and an outlet (12) at the bottom or side of the vessel, as long as the discharge of fluid does not affect the level of process fluid in the foam cell vessel; an inner foaming cup (10) that is shorter and smaller in diameter than the outer cylindrical vessel (8) and is suspended from about 1 centimeter (cm) to about 20 cm from the bottom of the outer cylindrical vessel (8). A tube or pipe (10) is suspended above the foaming cup and extends from the inlet to within about 1 cm to about 25 cm of the bottom of the foaming cup (10). However, the depth of the tube is dependent upon the velocity of the water flow and the depth of the cup itself.

Bubbles may form foam as air is entrained at the point where the downward flow of process fluid meets the fluid level in the cup section. The cup fills and the process fluid and foam cascade over the lip of the cup, where foam may accumulate on the fluid surface, which is maintained constant, within the outer vessel.

A non-contact optical distance measurement sensor (16) emits a light signal that is reflected off of the surface of the accumulated foam back to the optical sensor and the signal transferred to a microprocessor (19). The microprocessor then controls the amount of defoamer delivered to the fluid process.

The level of process fluid in the outer cylindrical vessel (8) in the current process is maintained at a constant level using an overflow (14), wherein the process fluid flows through an outlet (12) of the outer cylindrical vessel (8) through a trap pipe (13) to an overflow (14) thereby keeping a constant level of process fluid (15) in the outer cylindrical vessel. The overflow can be located anywhere on the foam cell vessel as long as it does not disrupt or affect the level of process fluid in the foam cell vessel or the generation of foam.

In still other aspects of the current method, the overflow (14) is the same height as the top of the foaming cup (10), thereby maintaining the fluid level at the top of the foaming cup (10) and the accumulating foam being above the rim of the foaming cup. The non-contact optical distance measurement sensor (16) can then be used to measure the foam height and control defoamer added accordingly.

The rate of process fluid flow of the side-stream into the foam cell vessel (8) can be regulated by the size of the pipe diameter of the inlet line used to transfer the process fluid from the fluid process stream (1) to the foam cell vessel (8) or other flow regulating means such as a valve, orifice or fluid pump speed (2).

In some aspects, a nozzle may also be installed on the inlet line to increase the velocity of the inlet water, which in turn entrains more air creating more foam with less water flow.

The foam cell vessel can discharge the process fluid from any outlet and the outlet can be at the bottom center of the foam cell vessel. However, as indicated above, the outlet may be located anywhere on the foam cell vessel so long as it does not disrupt the process fluid level being maintained or that it does not carry away the foam which is being accumulated within the vessel. The size of the discharge opening should be of sufficient diameter to cause little to no restriction in flow or elevation of the fluid level in the cell so as to keep the fluid level relatively constant in the foam cell vessel.

The fluid in the foam cell vessel may be intermittently charged with the process fluid, which may be subsequently recirculated or looped back into the foam cell vessel, by using for example, a pump, for a period of time until the next recharge cycle. The level of foam within the foaming vessel can be measured with the non-contact optical distance measurement sensor. The non-contact optical distance measurement sensor can then provide a continuous electronic output signal proportional to the level of foam in the foam cell vessel to a microprocessor. The proportional electronic level output signal, may be conditioned with the microprocessor to produce various control strategies with which to modify the feed of defoamer to strategic points in the process. Control strategies include but are not limited to proportional control through proportional-integral-derivative (PID) control as well as other timed feed strategies and manual response of the feed rate, based on the signal.

The rate of flow of the process fluid stream into the foam cell vessel can be controlled by, for example, by the size of the pipe diameter of the side-stream or a flow regulating method such as a flow control valve, orifice, nozzle or fluid pump speed. On/off cyclical flow may be used with recirculation systems, especially in systems which are subject to fouling by debris. The discharge of the process fluid from the foam cell vessel can be directly from the bottom of the vessel, and the outlet of sufficient diameter to cause little to no restriction in flow which can affect the fluid level in the foam cell vessel during normal operation. However, any point of outlet though may be used so long as it does not disrupt the water level being maintained or carry away the foam which is being accumulated within the foam cell vessel.

The defoamer can also be fed to the process fluid stream ahead of the sample point for the monitoring and control system. A side-stream of the process fluid is drawn or pumped through a sample line. In some cases, the process fluid can be passed through the foam cell vessel once, or the process fluid can be re-circulated through the vessel as many times or as long as necessary.

The materials used in the construction of the components of the foam cell vessel may be made of any suitable rigid material which is compatible with the process fluid.

In some aspects of the current methods, the outer or foam cell vessel can be cylindrical, can be square and may be rectangular in shape. Rectangular shaped vessels are useful for predicting how foam will accumulate in quiescent areas away from the foam generation site. Rectangular vessels can be used for simulating lagoon foam.

Other configurations are envisioned, such as those wherein the process fluid cascades into the foam cell vessel which maintains a constant fluid level.

In yet other aspects of the current method, an aspirator can be installed on the process fluid side-stream.

In the current process a constant water level may be achieved by a "fill and recirculate mode" wherein a sample of process fluid (7) is periodically drawn from the side-stream (3), as needed, using, for example automatically actuated valves (5), to purge and refill the foam cell vessel, the process fluid in the vessel can be discharged through an overflow/stand pipe (14), which acts as a trap of the newly drawn fluid, creating a constant fluid level in the cylinder or foam cell vessel (8) each time the unit undergoes an operation cycle. The discharge can also be accomplished by different means such as using automatically actuated valves. This method works well when there are foulants and debris in the fluid which would otherwise become trapped behind a flow throttling valve or orifice. As a result, larger transfer lines and fully open valve positions may be used.

The fluid level in the foam cell can also be maintained constant when a flow of the side-stream is drawn, as needed, and flows once-through the vessel and discharges through a line looping back up from the bottom of the outer or foam cell vessel through a stand pipe, creating a trap.

The foam cell vessel can be 20 centimeters and the discharge or outlet and overflow pipe may be in the size range of from a minimum of 2 centimeters diameter and larger. Different size cylinders, plumbing or vessels may be designed to suit the fluid characteristics of different processes. In general the outlet (12), trap pipe (13) and overflow (14) should be of sufficient diameter so as not to restrict the natural fluid flow thereby creating a substantially elevated fluid level.

In some aspects of the above methods, a recirculation loop may be added. Recirculation can be useful if the flow rate of the process fluid of the side-stream is insufficient to entrain air. Recirculation is also useful when the process fluid is drawn periodically at excessive flow and minor restriction to avoid line plugging by foulants and debris.

In other aspects of the methods, an optical distance sensor located above the foam cell continuously measures the foam level and converts the level into a proportional electronic level output signal. In yet other aspects, the device and method can further comprise one or more temperature, pH and conductivity sensors or probes. The device and method can also include, for example, a dehumidifying device used to control condensation in the sensing area.

The device and method can also include other sensors and devices to account for weather related elements that can affect the accumulation of foam in various water systems, such as the intensity of ambient sunlight, temperature, humidity, dewpoint, rainfall, and barometric pressure.

In some aspects of the above methods, during the initial set up, the monitoring and control system is calibrated to simulate the behavior of the fluid process under study by noting what level of foam height in the foam cell vessel corresponds to the maximum tolerable foam level in the process fluid stream. That level is then used to set the target control level set point of the microprocessor component of the control system. As the foam level in the foam cell vessel increases the microprocessor compares it to the distance from the set point and proportionally increases the defoamer feed rate to the process fluid stream so as to drive the foam level down. Should the foam level measured be below the set point, the controller systematically reduces the defoamer feed rate to allow foam to rise to the set point level.

The methods described above can be used in most fluid process streams which experience foaming and would benefit from monitoring and controlling the amount of defoamer or other additives being added to the system. Some examples include, flumes, trenches, tanks, ponds, pipelines, collection tanks, water chests, ponds and lagoons associated with food processing plants, pulp mills, paper mills, fermenters, and chemical plants. Other operations, include aerated tanks and basins associated with wastewater treatment systems, from collection systems through effluent pipes and flumes, including aerated activated sludge systems, in both industrial and municipal applications. Anaerobic and thermophilic digester type wastewater treatment systems are also candidates. Washing operations in pulp mills, food processing, algae processing, and mineral processing applications can all benefit. It may also be useful to control defoamer feed in open recirculating cooling water systems and process fluid cooling towers.

These methods would also be useful to control the dosages of foam causing additives such as frothing agents in a large variety of industrial processes, including but not limited to, mineral processing applications such as ore floatation and segregation, as well as deinking in paper recycling applications.

The above cited references are incorporated herein in their entirety.

EXAMPLES

A wastewater treatment plant of an integrated pulp and paper mill will generally experience problematic levels of highly foam forming substances such as surfactants, black liquor, soap and foul condensate, which find their way into the sewer system frequently, unpredictably, and in various quantities.

At the mill selected for the trial the wastewater flows by gravity from the primary clarifier outlet where the defoamer is added to a pump sump where three large pumps transfer the water uphill to a cooling tower which serves to cool the wastewater for the next stage in the treatment process. Foam formation problems have, in the past, expressed themselves on the surface of the pump sump, top of the cooling tower and cooling tower sump.

A defoamer is fed to wastewater treatment system at the outlet of the primary clarifier and the feed rate is adjusted approximately twice daily when the treatment plant operator makes his rounds. Normally if there is a high level of foam found during a spot in time that day, the defoamer feed rate is increased to as high as 100% and remains at that level until the next 12 hour shift.

The current method was used wherein a continuous side-stream sample of wastewater was drawn from the cooling tower feed pump at a discharge rate of 26.5 liters per minute. For infrequent periods when the mill has plastic in the wastewater stream, a course ¼ inch mesh basket strainer was installed in the feed line to prevent pluggage of the flow control valve. The waste water entered the foam cell vessel through a nozzle that directed the waste water into the center of a tube that extended into the foam cell vessel and was surrounded by an upward facing cup. As the wastewater hit the water level maintained by the cup, a mixture of air bubbles and water was generated and resulted in accumulation of foam on the surface of the water level within the foam cell vessel wherein the water level was kept constant. The path of the waste water side-stream was through the top of the foam cell vessel, reversing direction twice within the foam cell vessel. The downward force of the side stream of water entering the vessel and hitting the surface of the water in the inner cup, entrained air created a mix of water and air bubbles which flowed upward over the lip of the inner cup to the top the foam cell vessel, resulting in an accumulation of foam on the water surface around the inner perimeter of the vessel. The water level in the foam cell vessel was maintained constant while the foam level on top of the water was variable. The elevation of the wastewater level was maintained constant and in the proximity of the lip of the cup by a drain in the bottom of the foam cell vessel that was integrated with an external oversized standpipe that created a "U" shaped water flow path out of which water finally overflowed to drain. A Keyence Model LR-TB5000 Series All-Purpose Laser Sensor was positioned over the foam cell and tracked the foam level within it. The laser-sensor continuously produced an electrical output signal which was proportional to the distance of the foam level to the laser-sensor. The output signal was sent to a microprocessor where it was conditioned to reduce noise, scaled to the desired range of measurement evaluated, inverted, and finally used as a process variable in a proportional and integral control loop (PID) which controlled the output of the defoamer pump. The defoamer pump fed defoamer to the outfall of the primary clarifier where it was mixed with the waste water prior to the side-stream of waste water being diverted to the foam cell vessel.

The foam level was monitored and controlled within a narrow range of 61 cm to 76 cm from the Laser-Sensor: this resulted in a total range of 0 to 15 centimeters of total foam. During this period of time the defoamer pump ranged from 20% to 80% output to control the foam level at a target of 71 centimeters from the sensor. We were able to control the foam level in the target range with the proportional defoamer feed rate.

What is claimed:

1. A method for continuous on-line, real time, measurement, delivery and control of foaming of a process fluid comprising:
    providing a continuous stream of process fluid (1) as a side stream (3) to a foam cell vessel (8) having an inlet and outlet;
    maintaining a constant level of process fluid in the foam cell vessel by simultaneously draining through the outlet an equal amount of process fluid (1) from the foam cell vessel (8) as is entering the foam cell vessel (15); wherein the process fluid flows through the inlet and cascades into the foam cell vessel, thereby entraining air and creating a level of accumulated foam on the surface of the process fluid in the foam cell vessel (8); and wherein the outlet is configured so as not to disrupt the water level being maintained or carry away any accumulated foam in the foam cell vessel;
    measuring and monitoring the height of the accumulated foam using a non-contact optical distance measurement device (16) capable of providing an electronic output signal proportional to the level of foam in the foam cell vessel; and
    delivering a defoamer to the process fluid dependent upon whether the level of foam is below, at or above a pre-determined set point.

2. The method according to claim 1, further comprising introducing compressed air into the constant fluid level of the foam cell vessel or introducing air into the process fluid side stream.

3. The method according to claim 1, wherein the non-contact optical distance measurement sensor is a "reflective model-photoelectric sensor".

4. The method according to claim 1, where the foam cell vessel is cylindrical, conical, ovoid, sphere, conical flash, spherical flask, cube or box shaped.

5. The method according to claim 1, wherein a flow meter is used to monitor the fluid flow rate into or out of the foam cell vessel.

6. The method according to claim 1, further comprising one or more temperature, pH and conductivity sensors and probes.

7. The method according to claim 1, wherein a variable speed pump is used to deliver the process fluid side stream to the foam cell vessel.

8. The method according to claim 1, wherein a flow control valve is used to maintain a constant flow rate to the foam cell vessel.

9. The method of claim 1, further comprising adding pigments, dyes, and fluorescing agents to the process fluid side stream.

10. The method according to claim 1, wherein a dehumidifying device is used to control condensation in the sensing area.

11. The method according to claim 1, further comprising automatically actuated valves to periodically dump and refill the foam cell vessel.

12. The method according to claim 1, wherein the microprocessor uses any combination of proportional, integral or derivative (PID) control to control the defoamer feed.

13. The method according to claim 1, wherein an alarm sounds when no variation is detected in the foam height over a certain period of time.

14. The method according to claim 1, wherein the side-stream (3) of the process fluid (1) is recirculated through the foam cell vessel.

15. The method according to claim 1, wherein the side-stream (3) of the process fluid (1) is selected from the group consisting of an activated sludge aeration system, a pulp mill brown stock washer system, a paper machine system, an aerated settling basin, a waste water effluent stream, a trench leading to or from a wastewater treatment system, wastewater collection system, a wastewater treatment plant, a fermentation system, a washing or flume operation for food products, an open recirculating cooling water system, an air washer system, a once through cooling water system, a cooling system discharge to a waterway or pond, a mineral washing operation, a parts washing application, a mineral processing application, a mineral floatation and separation operation, a deinking frothing operation, an anaerobic or aerobic digester system, a fiberglass mat manufacturing water system, a wet scrubber system, an air stripping water system, and a thermophilic digester system.

16. A method for continuous on-line, real time, measurement, delivery and control of foaming of a process fluid stream comprising:
providing a side-stream (3) of the process fluid (1) to a foam cell vessel having an inlet and outlet; wherein the foam cell vessel comprises an inner cup (10), and a tube or pipe (9) that is suspended above and extends within the cup to about 1 cm to about 25 cm of the bottom of the inner cup (10);
directing the process fluid (1) of the side-stream (3) through the tube or pipe (9) into the inner cup (10) generating foam and foam accumulation (11);
maintaining a constant level of the process fluid in the foam cell vessel and inner cup (10) by monitoring the flow rate of the process fluid going into or from the foam cell vessel, and wherein the outlet is configured so as not to disrupt the water level being maintained or carry away any accumulated foam from the inner cup or the foam cell vessel;
emitting a signal from a non-contact optical distance measurement sensor (16), wherein the signal is reflected off of the surface of the foam and back to the measurement sensor (16);
transferring the signal to a microprocessor (19) that calculates the height of the accumulated foam based on the constant level of the process fluid (15) in the inner cup;
delivering a defoamer to the process fluid dependent upon whether the level of foam is below, at or above a pre-determined set point.

17. The method according to claim 1, wherein a microprocessor is used to calculate the accumulated foam and determine the amount of defoamer to add to the process fluid.

* * * * *